United States Patent [19]

Meul et al.

[11] Patent Number: 4,824,966

[45] Date of Patent: Apr. 25, 1989

[54] PROCESS FOR THE PRODUCTION OF 4-HYDROXY-2-OXO-PYRROLIDIN-1-YL ACETAMIDE

[75] Inventors: Thomas Meul; John McGarrity, both of Visp, Switzerland

[73] Assignee: Lonza Ltd., Gampel/Valais, Switzerland

[21] Appl. No.: 188,702

[22] Filed: May 4, 1988

Related U.S. Application Data

[63] Continuation of Ser. No. 905,128, Sep. 9, 1986, abandoned.

[30] Foreign Application Priority Data

Sep. 24, 1985 [CH] Switzerland ................. 4126/85
May 20, 1986 [CH] Switzerland ................. 2023/86

[51] Int. Cl.$^4$ ............................... C07D 207/27
[52] U.S. Cl. ...................................... 548/544
[58] Field of Search ............................ 548/544

[56] References Cited

U.S. PATENT DOCUMENTS 2,535,010 12/1950 Croxall et al. ............... 260/484
2,784,191 3/1957 Fischer et al. ............... 260/294.7
4,118,396 10/1978 Pifferi et al. ................ 548/544
4,124,594 11/1978 Monguzzi et al. ............ 548/544
4,173,569 11/1979 Banfi et al. .................. 548/544

FOREIGN PATENT DOCUMENTS 192255 2/1985 European Pat. Off. .
850007 9/1952 Fed. Rep. of Germany .
57-183756 4/1981 Japan .

OTHER PUBLICATIONS

MacKenzie et al., J.O.C.S., 20, No. 12, (1955), pp. 1695 and 1696.
Koehler, Dissertation Bayreuth, (1985).
G. Pifferi et al., Il Farmaco, Ed. Sc., 1977, 32, 602.
Sidgwick, "The Organic Chemistry Of Nitrogen", 3rd Ed., Oxford, (1966), p. 637.
Ho et al., "Cleavage of Esters And Ethers With Iodotrimethylsilane" Angewandte Chemie, vol. 15, No. 12, (Dec. 1976), pp. 774 and 775.
Cram et al., J. Am. Chem. Soc., 1963, 85, 1430-1437.
Chemical Abstracts, vol. 52, 11124g.
Lowe, J. Chem. Soc., Perkin Trans. I, 1973, 2907-2910.

Primary Examiner—Glennon H. Hallrah
Assistant Examiner—David B. Springer
Attorney, Agent, or Firm—Fisher, Christen & Sabol

[57] ABSTRACT

Process for the production of 4-hydroxy-2-oxo-pyrrolidin-1-yl acetamide. A 4-($C_1$-$C_2$)-alkoxy-3-pyrrolin-2-on-1-yl-acetic acid ($C_1$-$C_4$)-alkyl ester of the formula:

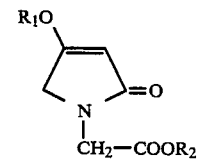

wherein $R_1$ is alkyl having 1 or 2 C atoms and $R_2$ is alkyl having 1 to 4 C atoms, is reacted with either trichloromethylsilane in the presence of an alkali iodide or in an acid anhydrous medium to a 2,4-dioxo-pyrrolidin-1-yl-acetic acid ($C_1$-$C_4$)-alkyl ester. The latter is optionally isolated and then hydrogenated with sodium borohydride to a 4-hydroxy-2-oxo-pyrrolidin-1-yl-acetic acid ($C_1$-$C_4$)-alkyl ester. Finally, the 4-hydroxy-2-oxo-pyrrolidin-1-yl-acetic acid ($C_1$-$C_4$)-alkyl ester is converted by amidation with ammonia to the desired end product.

5 Claims, No Drawings

PROCESS FOR THE PRODUCTION OF 4-HYDROXY-2-OXO-PYRROLIDIN-1-YL ACETAMIDE

This application is a continuation of application Ser. No. 905,128, filed Sept. 9, 1986, abandoned.

BACKGROUND OF THE INVENTION

1. Field of the Invention

The invention relates to the production of cerebrally-effective 4-hydroxy-2-oxo-pyrrolidin-1-yl acetamide.

2. Prior Art

Pifferi et al., Il Farmaco, Ed. Sc., 1977, 32, 602, discloses producing 4-hydroxy-2-oxo-pyrrolidin-1-yl acetamide in five stages. However, costly starting products and a total yield of about 33.8 percent make such process unprofitable.

BROAD DESCRIPTION OF THE INVENTION

The main object of the invention is to provide a production method that does not exhibit the above-noted disadvantages. Other advantages and objects of the invention are set out herein or are obvious herefrom to one skilled in the art.

The objects and advantages of the invention are achieved by the process of the invention.

The invention involves a process for the production of 4-hydroxy-2-oxo-pyrrolidin-1-yl acetamide. The process includes reacting a 4-($C_1$-$C_2$)-alkoxy-3-pyrrolin-2-on-1-yl-acetic acid ($C_1$-$C_4$)-alkyl ester of the formula:

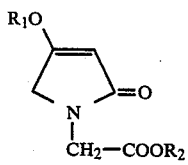

wherein $R_1$ is alkyl having 1 or 2 C atoms and $R_2$ is alkyl having 1 to 4 C atoms, is reacted with either trichloromethylsilane in the presence of an alkali iodide or in an acid anhydrous medium to a 2,4-dioxo-pyrrolidin-1-yl-acetic acid ($C_1$-$C_4$)-alkyl ester. The latter is optionally isolated and then hydrogenated with sodium borohydride to a 4-hydroxy-2-oxo-pyrrolidin-1-yl-acetic acid ($C_1$-$C_4$)-alkyl ester. Finally, the 4-hydroxy-2-oxo-pyrrolidin-1-yl-acetic acid ($C_1$-$C_4$)-alkyl ester is converted by amidation with ammonia to the desired end product.

If the process is conducted according to the first variant with trichloromethylsilane and with an alkyli iodide the molar ratio of the starting compounds is advantageously as follows. 4-($C_1$-$C_2$)-alkoxy-3-pyrrolin-2-on-1-yl-acetic acid ($C_1$-$C_4$)-alkyl ester to trichloromethylsilane to alkali iodide advantageously between 1 to 1 to 1 and 1 to 2 to 2 preferably between 1 to 1.2 and 1 to 1.6.

DETAILED DESCRIPTION OF THE INVENTION

The preferred alkali iodide is sodium iodide. The preferred 4-($C_1$-$C_2$)-alkoxy-3-pyrrolin-2-on-1-yl-acetic acid ($C_1$-$C_4$)-alkyl ester is 4-methoxy-3-pyrrolin-2-on-1-yl-acetic acid ethyl ester.

Advantageously, the reaction is performed in acetonitrile as solvent, although any suitable solvent can be used. The reaction temperature is preferably in the range of the reflux temperature of the solvent. After a reaction time of about 1 to 5 hours and the usual working up, such as, by extraction and optionally by subsequent purification of the product, i.e., by recrystallization, the corresponding 2,4-dioxo-pyrrolidin-1-yl-acetic acid ($C_1$-$C_4$)-alkyl ester is obtained.

If the process is conducted according to the second variant in an acid anhydrous medium, the procedure advantageously is as follows. The acid medium is advantageously produced by the introduction of gaseous hydrochloric acid or gaseous hydrogen bromide into a ($C_1$-$C_4$)-carboxylic acid, which is also anhydrous. The preferred ($C_1$-$C_4$)-carboxylic acid is acetic acid. Use of gaseous hydrochloric acid in acetic acid is especially preferred. The reaction temperature is advantageously chosen between 0° to 50° C. After a reaction time of 5 to 10 hours the reaction mixture can be worked up in the usual way, e.g., by evaporation of the solvent and optionally by crystallization.

The conversion of the 2,4-dioxo-pyrrolidin-1-yl-acetic acid ($C_1$-$C_4$)-alkyl ester, especially the ethyl ester, into the desired 4-hydroxy-2-oxo-pyrrolidin-1-yl acetamide by reduction with sodium borohydride and subsequent amidation with ammonia has already been shown in the literature. [G. Pifferi and M. Pinza, Il Farmaco, Ed. Sc., 1977, 32, 602.] The 4-hydroxy-2-oxo-pyrrolidin-1-yl acetamide is then obtained as a pure white product in a good yield.

EXAMPLE 1

(a)

Production of 2,4-dioxo-pyrrolidin-2-on-1-yl ethyl acetate 2.0 g (10 mmol) of 4-methoxy-3-pyrrolin-2-on-1-yl ethyl acetate and 2.1 g (14 mmol) of sodium iodide were dissolved in 20.0 ml of acetonitrile. Then 1.6 g (14 mmol) of methyltrichlorosilane were added. The yellowish colored cloudy solution was heated for 4 hours with reflux. It was allowed to cool to room temperature and the solvent was evaporated with water jet vacuum. The residue was suspended in 50.0 ml of methylene chloride and mixed with a solution of 1.0 g of sodium bisulfite in 5.0 ml of ice water. The aqueous phase was extracted three times, each time with 50.0 ml of methylene chloride. The combined organic phases were dried over $Na_2SO_4$, evaporated and dried in a high vacuum. 1.9 g of an orange colored mass, which slowly crystallized throughout, was obtained. The recrystallized product (toluene:petroleum ether 1:1) melted at 92° to 93° C.

NMR ($CDCl_3$) δ=4.25 (s, 2H); 4.23 (q, J=7.1 Hz, 2H); 4.03 (t, J=1.0 Hz, 2H); 3.11 (br. s, 2H); 1.30 (t, J=7.1 Hz, 3H).

(b)

Production of 4-hydroxy-2-oxo-pyrrolidin-1-yl ethyl acetate 0.54 g (14.5 mmol) of sodium borohydride was added to 8.8 g (47.5 mmol) of 2,4-dioxo-pyrrolidin-1-yl ethyl acetate in 200 ml of dimethoxyethane. The mixture was stirred for one hour at room temperature. After cooling to 0° C., excess concentrated hydrochloric acid was added and the inorganic residue was filtered. The filtrate was evaporated to dryness. The residue was taken up in chloroform, dried over $Na_2SO_4$ and again evaporated under vacuum. 8.8 g of the product in oil form resulted. A subsequent distillation at 180° C./1.0 mbar led to 5.3 g (60 percent) of a colorless oil.

IR (film) 3400 cm$^{-1}$ (OH), 1740 cm$^{-1}$ (C=O), 1680 cm$^{-1}$ (C=O), 1200 cm$^{-1}$.

(c)

Production of 4-hydroxy-2-oxo-pyrrolidin-1-yl acetamide 13.7 g (73 mmol) of 4-hydroxy-2-oxo-pyrrolidin-1-yl ethyl acetate was dissolved in 500 ml of methanol and saturated with ammonia at 0° C. Then it was kept at room temperature for an hour. Evaporation of the solvent under vacuum lead to a solid residue. This residue was crystallized in methanol. 7.17 g (62 percent) of the product in the form of a white powder resulted. Melting point: 165° to 168° C.

IR (Nujol) 3400 cm$^{-1}$, 3300 cm$^{-1}$, 3250 cm$^{-1}$ (OH and NH), 1660 cm$^{-1}$ (C=O).

EXAMPLE 2

(a)

Production of 2,4-dioxo-pyrrolidin-1-yl ethyl acetate 10.0 g of 4-methoxy-3-pyrrolin-2-on-1-yl ethyl acetate (GC content: 80 percent) was dissolved in 50.0 ml of acetic acid and saturated with gaseous hydrochloric acid at 35° to 40° C. for 9 hours with stirring. Then the acetic acid was evaporated on a rotary evaporator under vacuum at a bath temperature of 60° C. The residue was taken up in 50.0 ml of toluene and once again evaporated. 12.4 g of raw product, which crystallized when placed in a refrigerator, remained.

(b)

Production of 4-hydroxy-2-oxo-pyrrolidin-1-yl ethyl acetate 12.2 g of the raw product obtained above was dissolved in 50.0 ml of acetonitrile and, at room temperature, added to a suspension of 1.6 g of sodium borohydride in 50.0 ml of acetonitrile. Thus, the reaction temperature rose to 35° to 40° C. At this temperature the reaction solution was stirred for another hour. Then it was acidified with concentrated hydrochloric acid to a pH of about 5. The solvent was concentrated in a rotary evaporator. The residue was mixed with 25.0 ml of ice water and extracted with methylene chloride. After drying of the methylene chloride solution over sodium sulfate and evaporation of the solvent, 9.5 g of raw product with a content of 51.5 percent according to HPLC remained. This corresponded to a yield of 66.1 percent in relation to the 4-methoxy-3-pyrrolin-2-on-1-yl ethyl acetate used. Chromatographic filtration over silica gel with acetic acid as the mobile solvent resulted in a product with a content greater than 96 percent (HPLC).

The production of the 4-hydroxy-2-oxo-pyrrolidin-1-yl acetamide was performed according to Example 1(c).

What is claimed is:

1. Process for the production of 4-hydroxy-2-oxo-pyrrolidin-1-yl acetamide comprising (a) reacting 4-($C_1$–$C_2$)-alkoxy-3-pyrrolin-2-on-1-yl-acetic acid ($C_1$–$C_4$)-alkyl ester of the formula:

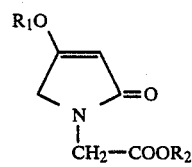

wherein $R_1$ is alkyl having 1 or 2 C atoms and $R_2$ is alkyl having 1 to 4 C atoms, with trichloromethyl-silane in the presence of an alkali iodide to a 2,4-dioxo-pyrrolidin-1-yl-acetic acid ($C_1$–$C_4$)-alkyl ester, (b) hydrogenating the 2,4-dioxopyrrolidin-1-yl-acetic acid ($C_1$–$C_4$)-alkyl ester with sodium borohydride to a 4-hydroxy-2-oxo-pyrrolidin-1-yl-acetic acid ($C_1$–$C_4$)-alkyl ester, and (c) converting the 4-hydroxy-2-oxo-pyrrolidin-1-yl-acetic acid ($C_1$–$C_4$)-alkyl ester by amidation with ammonia to said acetamide.

2. Process according to claim 1 wherein sodium iodide is used as alkali iodide.

3. Process according to claim 2 wherein the reaction (a) with trichlormethylsilane in the presence of sodium iodide takes places additionally in the presence of acetonitrile as a solvent.

4. Process according to claim 1 wherein the reaction (a) with trichlormethylsilane in the presence of an alkali iodide takes places additionally in the presence of acetonitrile as a solvent.

5. Process according to claim 1 wherein the 2,4-dioxo-pyrrolidin-1-yl-acetic acid ($C_1$–$C_4$)-alkyl ester is isolated from the reaction mixture of step (a) before it is hydrogenated.

* * * * *